United States Patent

Bernhard et al.

Patent Number: 5,780,693
Date of Patent: Jul. 14, 1998

[54] PROCESS FOR THE MANUFACTURING OF ZEAXANTHIN FROM LUTEIN

[75] Inventors: Kurt Bernhard, Lupsingen; Alfred Giger, Möhlin, both of Switzerland

[73] Assignee: Roche Vitamins Inc., Parsippany, N.J.

[21] Appl. No.: 935,262

[22] Filed: Sep. 22, 1997

[30] Foreign Application Priority Data

Oct. 4, 1996 [EP] European Pat. Off. ............ 961159084

[51] Int. Cl.$^6$ .................................................. C07C 35/21
[52] U.S. Cl. ........................................................ 568/816
[58] Field of Search ............................. 568/816, 834, 568/822, 823, 828, 824, 832

[56] References Cited

U.S. PATENT DOCUMENTS

| | | |
|---|---|---|
| 3,523,138 | 8/1970 | Grant . |
| 3,535,138 | 10/1970 | Wanmaker et al. . |
| 3,783,099 | 1/1974 | Matoushek . |

FOREIGN PATENT DOCUMENTS

| | | |
|---|---|---|
| 1 046 658 | 10/1966 | United Kingdom . |
| 96/02594A2 | 2/1996 | WIPO . |
| 97/31894 | 9/1997 | WIPO . |

OTHER PUBLICATIONS

Jucker et al., Helv. Chim. Acta, 30: 266–267 (1947).
Kargl et al., "The Structure of δ–Carotene", Arch. Biochem. Biophys. 88:59–63 1960).
Zucker et al. ". . . ", Chimia 26, No. 3, pp.134–136 (1972).
A. G. Andrews, "Isomerization of ε–Carotene to β–Carotene and of Lutein to Zeaxanthin", Acta. Chem. Scand. B 28, No. 1, pp. 137–138 (1974).

Quakenbush et al., "Composition and Analysts of the Carotenoids in Marigold Petals", Journal of the AOAC. vol. 55, No. 3, pp. 617–621 (1972).

Gau et al., "Mass Spectrometric Identification of Xanthophyll Fatty Acid Esters From Marigold Flowers (*Tagetes Erecta*)Obtained by High–Performance Liquid Chromatography and Craig Counter–Current Distribution", Journal of Chromatography 262:277–284 (1983).

Derwent Abstract No. 97–47053 of WO 97/31894.

Derwent Abstract No. 96–167352 of JP 8048895.

*Primary Examiner*—Gary Geist
*Assistant Examiner*—Karl J. Puttlitz, Jr.
*Attorney, Agent, or Firm*—George W. Johnston; Dennis P. Tramaloni; Bruce A. Pokras

[57] ABSTRACT

A process for the conversion of lutein or of its esters into zeaxanthin by base-catalyzed isomerization is disclosed. The process is carried out by heating an optionally pretreated lutein-containing material in a mixture of an aqueous solution of an alkali hydroxide and either dimethyl sulphoxide or an organic solvent based on saturated aliphatic and/or aromatic hydrocarbons at temperatures in the range from about 50° C. to about 120° C. The process is carried out in the presence of a phase transfer catalyst when an organic solvent based on hydrocarbons is used. Being carotenoids, lutein and zeaxanthin are used correspondingly, especially as pigments for egg yolk, the integuments and the subcutaneous fat of poultry, the flesh and the integuments of fish and crustaceans, as well as foodstuffs. Zeaxanthin is preferably used in many applications, since in comparable dosages it produces a more intensive golden yellow pigmentation than lutein.

17 Claims, No Drawings

PROCESS FOR THE MANUFACTURING OF ZEAXANTHIN FROM LUTEIN

BACKGROUND OF THE INVENTION

The present invention is concerned with a process for the conversion of xanthophylls, especially of lutein into zeaxanthin.

As is known, the xanthophylls lutein and zeaxanthin belong to the broad substance class carotenoids and as natural pigments are widely distributed in nature. They are present primarily in higher plants, algae, fish, crustaceans and bacteria. Lutein and zeaxanthin are often found together and in esterified form in the same source, although the ratio of lutein to zeaxanthin varies substantially depending on the source. Thus, lutein normally makes up a substantially larger amount than zeaxanthin when they occur together in plants, e.g., melons and marigolds [Tagetes (T.) erecta, T. patula and other Tagetes species] and in algae. As an exception there is to be mentioned the larger amount of zeaxanthin over lutein in maize, with the former being even the main representative of carotenoids present in maize grain. Moreover, the stereoisomerism of lutein and of zeaxanthin depends on the source. In plants sources (3R,3'R,6'R)-lutein or (3R,3'R)-zeaxanthin is primarily present, while in animal sources, e.g., in fish and crustaceans, lutein is present in the (3R,3'R,6'R)-, (3R,3'R,6'S)- and (3R,3'S,6'S)-form and zeaxanthin is present in the (3R,3'S)-and (3S,3'S)-form.

Being carotenoids, lutein and zeaxanthin are used correspondingly, especially as pigments, e.g., for egg yolk, the integuments (for example, skin, legs and beak) and the subcutaneous fat of poultry, the flesh and the integuments (skin, scales and shell) of fish and crustaceans as well as food-stuffs. Zeaxanthin is preferably used in many applications, since in comparable dosages it produces a more intensive golden yellow pigmentation than lutein.

When use is made of a plant raw material containing the two xanthophylls, such as, for example Tagetes erecta flowers, or of an optionally previously saponified extract thereof, as the source of the desired zeaxanthin, it is clearly economically more convenient, where possible, firstly to chemically convert the lutein into the zeaxanthin and then to isolate the latter from the mixture by extraction than to undertake the extraction without prior conversion. It is also of economical significance to chemically convert pure or almost pure lutein into zeaxanthin.

As is known, the conversion of lutein into zeaxanthin can be effected under strongly basic conditions, and a variety of pertinent conversion processes have become known from the scientific literature. Already in the year 1946 Karrer and Jucker realized the isomerization of natural lutein (referred to as "xanthophyll") to zeaxanthin in an ethanol-benzene mixture by heating at 110°–110° C. with sodium ethanolate for 30 hours in an evacuated bomb tube [see Helv. Chim. Acta 30, 266–267 (1947)]. The yield of zeaxanthin was, however, extremely low. In this manner, no doubt for the first time, lutein, of the formula:

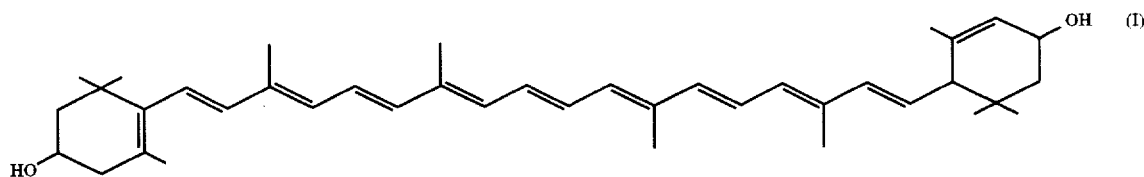

(without details of the configuration), was intentionally chemically converted into zeaxanthin, of the formula:

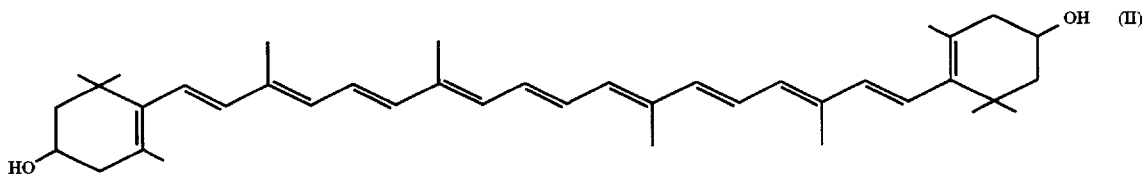

,with the isolated double bond in the ε-ring [(I), right] being brought into conjugation with the remaining double bonds of the molecule [(II), right: β-ring].

Later [1959, see Arch. Biochem. Biophys. 88, 59–63 (1960)], Kargl and Quackenbush accomplished the analogous base-catalyzed conversion of δ-carotene (ε,ψ-carotene) into γ-carotene (β,ψ-carotene). However, Buchecker et al. were unable to satisfactorily repeat the earlier work of Karrer and Jucker [Chimia 26, No. 3, 134–136 (1972)]. Andrewes reported in Acta Chem. Scand. B 28, No. 1, 137–138 (1974) the isomerization of lutein to zeaxanthin by heating a solution of lutein and potassium methanolate in methanolic dimethyl sulphoxide at 118° C. for 20 minutes in a closed tube under nitrogen, which gave a yield of only 10–15%. In a subsequent article (ibid. p. 139–140) Andrewes, Borch and Liaaen-Jensen showed that this isomerization was the conversion of (3R,3'R,6'R)-lutein into (3R,3'S)-zeaxanthin. Disadvantageous in the method of Andrewes was not only the still unsatisfactory yields of zeaxanthin, but also the finding established as a result of a re-working that numerous (Z)-isomers of not only zeaxanthin but also lutein are produced and that the reaction is therefore non-selective. Moreover, an isomerization which is effected in a closed reaction vessel is a reaction which cannot readily be controlled. Even when the conversion is carried out in an open system under argon it turns out that, after using potassium methylate as the base as previously, an uncontrollable (E)→(Z) isomerization takes place.

A further relevant publication, namely PCT Patent Publication WO 96/02594, has recently appeared. This describes a process for the isomerization of lutein to zeaxanthin in a strongly alkaline solution under controlled temperature and pressure conditions. The base is an alkali metal hydroxide, calcium hydroxide, sodium carbonate, ammonium hydroxide or an organic base, especially ethylamine, ethanolamine or morpholine. A solvent other than water is not used. An enrichment of the zeaxanthin from 4.5% (in the educt) to 15.8 to 24.0% has been said to be achieved by this process; it is, however, not mentioned how many decomposition products result in the isomerization. Also, this yield is not adequate for commercial purposes.

SUMMARY OF THE INVENTION

The aim of the present invention is to enrich the content of zeaxanthin or to manufacture zeaxanthin in the highest possible yields starting from a natural product containing the two xanthophylls lutein and zeaxanthin (in each case optionally in esterified form), or from pure or almost pure lutein. It has now surprisingly been found that this object can be achieved by a particular choice of reaction conditions, especially the choice of solvent and base. The yields of zeaxanthin can be decisively improved by this choice.

DETAILED DESCRIPTION OF THE INVENTION

The present invention provides a process for the conversion of lutein or its esters occurring in nature into zeaxanthin by base-catalyzed isomerization, which process comprises heating a lutein-containing material, which may be an optionally pre-treated natural lutein-containing product or pure lutein, in a mixture of an aqueous solution of an alkali hydroxide and either dimethyl sulphoxide ("DMSO") or an organic solvent based on saturated aliphatic and/or aromatic hydrocarbons at temperatures in a range from about 50° C. to about 120° C., with the process being carried out in the presence of a phase transfer catalyst when an organic solvent based on hydrocarbons is used.

As used herein, the lutein-containing material may be pure lutein, or any material containing lutein or esters thereof. Especially preferred lutein-containing materials are natural materials which contain lutein or esters thereof and other xanthophylls such as zeaxanthin.

As the natural lutein-containing material there is preferably used a lutein-containing raw material of plant origin, which optionally has been pre-treated chemically, e.g., by saponification, to produce free lutein from the esters thereof. Such a raw material can be a concentrate or extract which is present in the form of a milled powder or a liquid or resinous material ("oleoresin"). Powders or extracts of the yellow or orange blossoms of marigolds (e.g., *Tagetes erecta*, etc.), which contain not only lutein but also zeaxanthin, are the especially preferred lutein-containing materials.

According to Quackenbush et al. [J.AOAC, 55 (3), 617–621 (1972)] the lutein:zeaxanthin ratio in these raw materials is about 72–88:16–4. The xanthophylls present are mainly esters of palmitic, myristic and stearic acid [W. Gau et al., J. Chromatography 262, 277–284 (1983)]. Since it is preferred to convert the lutein to the free form prior to carrying out the process of the invention, such esters are preferably previously saponified to the free lutein before the lutein-containing material is used in the process in accordance with the invention. Such saponifications, as well as enzymatic hydrolyses carried out for the same purpose, may be carried out by any conventional means and are known in the art (see, for example, U.S. Pat. Nos. 3,535,138 and 3,783,099).

Powder (flour) and saponified and non-saponified extracts of *Tagetes* have been available commercially for a long time, and can be used as starting materials for the process in accordance with the invention. Examples of these raw materials are saponified Tagetes extracts from the Mexican firms ALCOSA and IOSA. The ALCOSA product "pasta saponificada amarillo" is a brownish paste having a total xanthophyll content of, for example, about 2.7%, consisting of about 92.5% lutein and about 6.6% zeaxanthin, while the IOSA product "HI-GOLD 20" is a greenish-yellow powder, which contains, for example, about 0.96% total xanthophylls (about 65.5% lutein and about 27.2% zeaxanthin) (the percentages are area percentages). These details have been established following the analysis of certain production batches and can vary from batch to batch, which also applies to the analytical results given hereinafter.

Other raw materials are "FLORA GLO"[Kemin Ind., Iowa, U.S.A.; about 739 g/kg total xanthophylls, of which about 681 g/kg consists of (all-E)-lutein and about 58 g/kg consists of (all E)-zeaxanthin], "ORO GLO Layer dry" (esterified, i.e., non-saponified; likewise Kemin Ind.; about 19.4 g/kg total xanthophylls: about 17.6 g/kg lutein and about 1.8 g/kg zeaxanthin), "HI-GOLD 20 Lutexan" (IOSA; about 16.3 g/kg total xanthophylls: about 11.0 g/kg lutein and about 5.3 g/kg zeaxanthin) as well as "XANTOPINA PLUS" (esterified; Bioquimex S.A., Mexico; about 351 g/kg total xanthophylls: about 330 g/kg lutein and about 21 g/kg zeaxanthin).

The lutein-containing material can be processed before use by any conventional means, if desired, in order to concentrate the xanthophylls, for example by extraction, followed by chromatography and optionally also subsequent crystallization. A typical concentration method comprises extracting the raw material with acetone, subjecting the extract to flash chromatography on silica gel using a hexane/ethyl acetate mixture and then pure ethyl acetate as the eluting agent, concentrating the fractions obtained and crystallizing the solid resulting therefrom, e.g., from a mixture of methylene chloride and methanol. By using this method it has been possible to obtain, for example, from 100 g of "pasta saponificada amarillo"(ALCOSA; containing about 2.7% total xanthophylls) about 2.4 g of crystalline material consisting of about 93% (all-E)-(3R,3'R,6'R)-lutein and about 7% (all-E)-(3R,3'R)-zeaxanthin. This product is an example of a pre-treated natural lutein-containing material.

An organic solvent based on saturated aliphatic and/or aromatic hydrocarbons is used as the solvent in the process in accordance with the invention as an alternative to dimethyl sulphoxide. This is especially a liquid alkane or an aromatic hydrocarbon, including a mixture of two or more of these hydrocarbons, e.g., a mixture of several liquid alkanes, of several aromatic hydrocarbons or of one or more of such alkanes with one or more aromatic hydrocarbons. The liquid alkane is preferably a straight-chain or branched alkane with at least 5 carbon atoms, more preferably with 5–10 carbon atoms, such as, for example, pentane, hexane or heptane. Petroleum ether, preferably high-boiling petroleum ether, is an especially suitable alkane mixture and benzene and toluene are especially suitable aromatic hydrocarbons. The most preferred hydrocarbons are hexane, heptane and high boiling petroleum ether.

As is known, dimethyl sulphoxide is soluble in water, and thus an aqueous-organic solution readily forms with the aqueous alkali hydroxide solution which is also used. In contrast thereto, the alkanes and aromatic hydrocarbons are sparingly soluble in water, and thus when they are used a phase transfer catalyst must be employed.

The alkali hydroxide is preferably sodium hydroxide or potassium hydroxide, most preferably the latter. The concentration of the alkali hydroxide in the aqueous solution is at least 3 molar (M). Even aqueous solutions having concentrations up to saturation can be used. The concentration of the aqueous alkali hydroxide solution preferably lies in the range of about 7M to about 14M.

When a phase transfer catalyst is required in accordance with the process of the invention, any conventional phase transfer catalyst may be used. Tricaprylmethylammonium chloride (Aliquat® 336), tetra(n-butyl)ammonium hydrogen sulphate, various alkylbenzyldimethyl ammonium chlorides (benzalkonium chloride), benzyltri(n-butyl)ammonium bromide and tri(n-butyl)methylammonium iodide are examples of phase transfer catalysts used in accordance with the invention. Tricaprylmethylammonium chloride is preferably used as the phase transfer catalyst.

With respect to ratios, there are conveniently used per mol of (calculated) xanthophyll(s) in the lutein-containing material about 10 to about 450 mol of alkali hydroxide and where required about 0.5 to about 5 mol of phase transfer catalyst, preferably about 200 to about 250 mol of alkali hydroxide and, respectively, about 0.5 to about 1.5 mol of phase transfer catalyst. The dimethyl sulphoxide: aqueous alkali hydroxide solution volume ratio is generally about 4:1 to about 1:2, preferably about 2.5:1 to about 1:1. When an organic solvent based on saturated aliphatic and/or aromatic hydrocarbons is used, the respective organic solvent:aqueous alkali hydroxide solution volume ratio is generally about 8:1 to about 1:2, preferably about 4:1 to about 1:1. It follows that, having regard to these convenient ratios as well as other factors, especially the amount and composition of xanthophylls in the lutein-containing material, there are generally used about 50 to 300 ml of solvent-alkali hydroxide solution mixture per 10 g of lutein-containing starting material, preferably about 60 to 80 ml per 10 g.

Having regard to the fact that the formation of undesired byproducts and the decomposition of the desired zeaxanthin are promoted at too high temperatures and/or too long a reaction period, the conversion in accordance with the invention is carried out at temperatures which as far as possible do not exceed 120° C., i.e., the conversion is conveniently carried out at temperatures in the range of about 50° C. to about 120° C. Preferably, the conversion is carried out at temperatures in the range of about 80° C. to about 100° C.

The reaction period depends, inter alia, on the reaction temperature, the amount and concentration of aqueous alkali hydroxide solution and the amount and nature of the organic solvent used. In general, this period is about 5 to about 65 hours. However, the conversion preferably does not take longer than about 24 hours.

Under the above basic reaction conditions not only the lutein present in the lutein-containing material is converted into the desired zeaxanthin in good yield, but also the esters of lutein and/or zeaxanthin which may be present, e.g., the aforementioned palmitic, myristic and stearic esters, are for the most part converted into free zeaxanthin.

The working up of the mixture after completion of the conversion may be carried out by any conventional means. For example, the working up may be effected in a simple manner, conveniently by cooling the mixture to room temperature or about 0° C., optionally adding an alcohol, preferably methanol or ethanol, and filtering off the solid, which mainly consists of enriched zeaxanthin. Moreover, conventional purification techniques, such as, for example, extraction, column chromatography and recrystallization, can be used. The last three treatments are required especially when a phase transfer catalyst is used. A recrystallization which may be carried out is effected especially well using a mixture of methylene chloride and methanol.

The present invention is illustrated by the following Examples:

EXAMPLE 1

Pre-treatment of the starting material 300 g of "pasta saponificada amarillo" [Industrias ALCOSA S.A. DE C.V.; 23.9 g/kg (all-E)-lutein and 3.1 g/kg (all-E)-zeaxanthin] are suspended in 1.5 l of acetone and the suspension is stirred at room temperature for 30 minutes. Then, 200 g of Dicalite® (filter aid; Dicalite Europe Nord S.A.) are added thereto and the mixture is stirred for a further 5 minutes. The resulting suspension is then filtered through a layer of Dicalite®, the Dicalite® layer is suspended in 780 ml of acetone and the new suspension is stirred at room temperature for 30 minutes. After filtration of the suspension through a Dicalite® layer this is washed six times with 50 ml of acetone each time. The combined filtrates are concentrated under reduced pressure at 35° C., and in this manner there are obtained 143 g of a dark, red paste.

The paste is then subjected to a flash chromatography on 1 kg of silica (mesh 70–230) using 4 l of hexane/ethyl acetate (2:1), followed by 1.3 l of ethyl acetate. The ethyl acetate fraction is concentrated under reduced pressure at 35° C., which gives 20.6 g of a red, semi-crystalline oil. This oil is then crystallized from a methylene chloride/methanol mixture and the crystallizate is dried for 6 hours under a high vacuum at 37° C. In this manner there are obtained 6.36 g of a mixture of (all-E)-lutein and (all-E)-zeaxanthin (93:6 area percent) as dark red crystals.

EXAMPLE 2

Conversion of lutein into zeaxanthin

General procedure:

The solvent dimethyl sulphoxide or liquid alkane or alkane mixture is added to a lutein-containing material [for example, a mixture of lutein and zeaxanthin obtained according to Example 1, a commercially obtainable saponified, zeaxanthin-enriched Tagetes extract "oleoresina amarillo saponificada" (ALCOSA) or "HI GOLD 20" (IOSA), or a likewise commercially obtainable non-saponified Tagetes extract from the U.S. company Kemin Industries, Iowa] in a round flask equipped with a reflux condenser, stirrer and thermometer. When the liquid alkane or alkane mixture is used, the phase transfer catalyst is then added. Subsequently, the aqueous solution of the alkali hydroxide is added thereto and the reaction mixture is heated. In order to follow the course of the reaction, a sample of the reaction mixture (solution or suspension) can be removed periodically, diluted with methylene chloride, the methylene chloride solution washed to neutrality with saturated aqueous ammonium chloride solution and then with water, subsequently dried over anhydrous sodium sulphate and finally the solution subjected to a HPLC analysis.

After completion of the reaction has been established (no further conversion lutein→zeaxanthin) the homogeneous or heterogeneous solution is cooled to room temperature or 0° C. while stirring, with an alcohol, e.g., methanol or n-propanol, optionally being added during the stirring and cooling. The resulting suspension is filtered through a paper or glass fibre filter, the solid is washed several times with the chosen alcohol, is dried under a high vacuum at about 37° C. for at least one hour and, if desired, recrystallized from methylene chloride/methanol or methylene chloride/hexane.

Procedure and results using the starting material "oleoresina amarillo saponificada":

The starting material contains 23.9 g/kg lutein and 3.1 g/kg zeaxanthin. After extraction, chromatography and crystallization there is obtained a mixture which consists of 93.1% lutein, 6.6% zeaxanthin and 0.5% additional material. The results of the conversion carried out according to the above procedure are compiled in Table 1 hereinafter:

used as the organic solvent; in experiments (h) and (h') 300 mg of Aliquat® 336 are added.

In the case of experiment (a) the temperature is that of the heating bath; in all other cases the actual temperature of the reaction mixture is given.

Procedure and results with the starting material "oleoresina amarillo saponificada" (direct use)

TABLE 1

| Experiment designation | Lutein, amount | Solvent, amount | Base, conc., amount | Temperature | Reaction period (hours) | Di-(Z)-lutein | (all-E)-Lutein | (all-E)-Zeaxanthin | (Z) Lutein | (Z)-Zeaxanthin | Remarks |
|---|---|---|---|---|---|---|---|---|---|---|---|
| (a) | 10 mg | Hexane, 20 ml | NaOH, 17M, 5 ml | 85° C. | 2 | 5.1 | 5.8 | 25.1 | 5.7 | 25.9 | |
| (b) | 100 mg | Hexane, 20 ml | KOH, 7M, 5 ml | 64° C. | 15 | — | 18.0 | 79.6 | 0.2 | 0.9 | |
| (b') | | | | | | — | 15.8 | 83.1 | — | — | after crystallization from $CH_2Cl_2/CH_3OH$ |
| (c) | 100 mg | Hexane, 20 ml | KOH, 7M, 5 ml | 64° C. | 64 | — | 24.8 | 71.9 | — | — | |
| (c') | | | | | | — | 22.3 | 77.7 | — | — | after crystallization from $CH_2Cl_2/CH_3OH$ |
| (d) | 100 mg | Hexane, 20 ml | KOH, 10M, 5 ml | 64° C. | 15 | — | 19.3 | 75.7 | — | — | |
| (d') | | | | | | — | 12.3 | 87.7 | — | — | after crystallization from $CH_2Cl_2/CH_3OH$ |
| (e) | 100 mg | Heptane, 20 ml | KOH, 7M, 5 ml | 94° C. | 1.5 | 3.5 | 19.1 | 52.0 | — | 11.4 | |
| (e') | | | | | | — | 18.1 | 80.0 | — | — | After crystallization from $CH_2Cl_2/CH_3OH$ |
| (f) | 100 mg | Petroleum ether (high boiling), 15 ml | KOH, 7M, 5 ml | 84° C. | 1.5 | — | 21.5 | 66.2 | — | 4.2 | |
| (f') | | | | | | — | 16.0 | 84.0 | — | — | After crystallization from $CH_2Cl_2/hexane$ |
| (g) | 100 mg | Hexane, 10 ml | KOH, 11.5M, 5 ml | 64° C. | 4.5 | — | 11.3 | 72.5 | — | 3.4 | |
| (g') | | | | | | — | 6.6 | 93.4 | — | — | After crystallization from $CH_2Cl_2/CH_3OH$ |
| (g") | | | | | | — | 4.5 | 95.5 | — | — | After further crystallization from $CH_2Cl_2/hexane$ |
| (h) | 420 mg | hexane, 42 ml | KOH, 11.5M, 21 ml | 66° C. | 4.5 | — | 22.3 | 73.4 | 0.3 | 1.9 | |
| (h') | | | | | | — | 21.4 | 77.1 | — | — | After crystallization from $CH_2Cl_2/CH_3OH$ |

Additional remarks:

In all cases with the exception of experiments (h) and (h') 100 mg of Aliquat® 336 (Fluka Chemi AG, Buchs, Switzerland) are added to the reaction mixture as the phase transfer catalyst, since hexane, heptane or petroleum ether is The starting material has the above composition and is not extracted, chromatographed and crystallized, but used immediately. The results of the conversion (without phase transfer catalyst) carried out according to the above procedure are compiled in Table 2 hereinafter:

TABLE 2

| Experiment designation | Amount of starting material used | Solvent, amount | Base concn., amount | Temperature of the reaction mixture | Reaction period (hours) | Relative product composition | | | | | Remarks |
|---|---|---|---|---|---|---|---|---|---|---|---|
| | | | | | | Di-(Z)-lutein | (all-E)-Lutein | (all-E)-Zeaxanthin | (Z)-Lutein | (Z)-Zeaxanthin | |
| (i) | 10 g | Dimethyl sulphoxide, 40 ml | Potassium hydroxide, 14.3M, 20 ml | 95° C. | 2.5 | — | 6.2 | 29.0 | 16.6 | 24.6 | |
| (i') | | | | | | — | 4.5 | 31.8 | 20.8 | 27.5 | After crystallization from $CH_2Cl_2$/hexane |

Procedure and results with the starting material FLORA GLO

The starting material has a relative (percentage) composition of 91.3% (all-E)-lutein and 6.6% (all-E)-zeaxanthin and a total xanthophyll content of 73.9% (739 g/kg crude material). This material is already saponified, so that the probability of side-reactions is low. According to the above procedure (without phase transfer catalyst) the crude material is stirred in a mixture of dimethyl sulphoxide (DMSO) and concentrated aqueous potassium hydroxide solution (KOH) at about 80° C. or above this temperature. It is noticeable that the reaction takes place very cleanly, i.e. practically from educt to product. Also, the working up of the reaction solution is simple: the lutein-zeaxanthin mixture crystallizes from the solution (cooled to 0° C.) and is easily filtered off and rinsed with water in order to remove for the most part traces of excess base. The results of the conversion carried out in this manner are compiled in Table 3 hereinafter:

TABLE 3

| Experiment designation | Amount of starting material used | Solvent, amount | Base, conc., amount | Temperature of the reaction mixture | Reaction period (hours) | Relative (%) product composition | | | | | Product amount |
|---|---|---|---|---|---|---|---|---|---|---|---|
| | | | | | | (all-E)-Lutein[1] | (all-E)-Zeaxanthin[1] | Anhydro-lutein[2] | (all-E)-Lutein[3] | (all-E)-Zeaxanthin[3] | |
| (j) | 10.0 g | DMSO, 40 ml | KOH, 9.5M, 19 ml | 65° C. | 17 | 63.8 | 33.9 | | | | 7.185 g |
| (k) | 10.0 g | DMSO, 40 ml | KOH, 10.7M, 20 ml | 77–78° C. | 0.5 | 91.3 | 6.8 | | | | |
| | | | | | 1 | 89.4 | 7.9 | | | | |
| | | | | | 2 | 87.1 | 10.7 | | | | |
| | | | | | 4.3 | 82.9 | 14.6 | | | | |
| | | | | | 7 | 74.9 | 22.0 | | | | |
| | | | | | 23 | 34.2 | 59.4 | 4.2 | | | |
| | | | | | 28.5 | 33.9 | 61.7 | 3.9 | 21.0 | 42.1 | 7.67 g |
| (l) | 10.0 g | DMSO, 40 ml | KOH, 15M, 20 ml | 63–64° C. | 0.5 | 90.9 | 6.6 | | | | |
| | | | | | 1 | 88.0 | 6.4 | | | | |
| | | | | | 2 | 85.2 | 8.5 | | | | |
| | | | | | 4.3 | 82.5 | 15.1 | | | | |
| | | | | | 7 | 75.2 | 21.1 | | | | |
| | | | | | 22.5 | 50.3 | 46.4 | 1.7 | | | |
| | | | | | 28.5 | 50.4 | 47.4 | 1.7 | 42.1 | 36.7 | 8.16 g |
| (m) | 10.0 g | DMSO, 40 ml | KOH, 15M, 20 ml | 75–76°°C. | 0.5 | 80.5 | 15.1 | | | | |
| | | | | | 1 | 58.3 | 35.1 | 1.8 | | | |
| | | | | | 3.2 | 47.9 | 44.6 | 2.3 | | | |
| | | | | | 5 | 47.4 | 48.6 | 2.7 | | | |
| | | | | | 23 | 42.6 | 52.1 | 3.8 | | | |
| | | | | | 24 | 41.1 | 53.3 | 3.4 | 31.6 | 38.0 | 6.014 g |
| (n) | 10.0 g | DMSO, 80 ml | KOH, 10.7M, 40 ml | 80–82° C. | 18 | 24.0 | 68.4 | 5.1 | | | |
| | | | | | 23 | 24.9 | 68.2 | 5.3 | | | 7.045 g |
| (n') | 7.045 g | Recrystallization from $CH_2Cl_2$/MeOH | | | | | | Residue | 3.9 | 72 | 1.694 g |
| | | | | | | | | Mother liquor | 18.3 | 51.1 | 4.86 g |
| (o) | 10.0 g | DMSO, 80 ml | KOH, 10.7M, 20 ml | 82–85° C. | 16 | 29.2 | 56.1 | 8.0 | | | |
| | | | | | 23 | 27.8 | 60.1 | 9.1 | 14.1 | 30.8 | 5.6 g |
| (p) | 10.0 g | DMSO, 40 ml | KOH, 10.7M, 20 ml | 80–82° C. | 16 | 45.9 | 50.3 | 3.0 | | | 7.63 g |
| | | | | | 21.5 | 45.1 | 50.7 | 3.1 | | | |
| (q) | 5.0 g | DMSO, 20 ml | KOH, 10.7M, 10 ml | 80–83° C. | 6 | 29.6 | 68.0 | 2.4 | | | |
| | | | | | 22 | 28.8 | 68.2 | 2.4 | 16.5 | 44.2 | 4.86 g |
| (r) | 10.0 g | DMSO, 20 ml + 50 ml | KOH, 10.7M, 40 ml | 80–82° C. | 21 | 92.1 | 7.2 | | | | |
| | | | | | 42 | 74.4 | 22.2 | | | | |

TABLE 3-continued

| Experiment designation | Amount of starting material used | Solvent, amount | Base, conc., amount | Temperature of the reaction mixture | Reaction period (hours) | Relative (%) product composition | | | | | Product amount |
|---|---|---|---|---|---|---|---|---|---|---|---|
| | | | | | | (all-E)-Lutein[1] | (all-E)-Zeaxanthin[1] | Anhydrolutein[2] | (all-E)-Lutein[3] | (all-E)-Zeaxanthin[3] | |
| (s) | 10.0 g | DMSO, 40 ml | KOH, 10.7M, 20 ml | 93–95° C. | 23 | 24.9 | 71.3 | 3.9 | 19.5 | 55.1 | 7.223 g |
| (t) | 5.0 g | DMSO, 80 ml | KOH, 10.7M, 40 ml | 80–85° C. | 19 | 31.0 | 66.3 | 3.5 | 22.5 | 49.5 | 3.517 g |
| (u) | 10.0 g | DMSO, 40 ml | KOH, 10.4M, 20 ml + 10 ml | 80–82° C. | 5 | 45.1 | 50.5 | 2.9 | | | |
| | | | | | 23 | 43.0 | 53.7 | 2.5 | | | 11.3 g |
| (v) | 10.0 g | DMSO, 40 ml | KOH, 10.4M, 20 ml[4] | 82–84° C. | 3 | 31.4 | 63.7 | 4.9 | | | |
| | | | | | 21 | 26.7 | 67.4 | 5.9 | 16.2 | 15.5 | 3.61 g |
| (w) | 10.0 g | DMSO, 40 ml | KOH, 14.2M, 20 ml[5] | 107° C. | 0.5 | 14.1[6] | 79.4[6] | 6.6[6] | 8.8[6] | 35.2[6] | |
| | | | | | | 11.9 | 44.5 | 19.3 | | | |
| | | | | | 1 | 2.9 | 27.2 | 67.0 | 0.3 | 4.2 | |
| | | | | | | | 28.7 | 50.0 | | | |
| (x) | 5.5 g | DMSO, 22 ml | KOH, 14.3M, 11 ml | 98–99° C. | 0.5 | 27.8 | 70.3 | 1.9 | | | |
| | | | | | 1 | 24.3 | 74.1 | 1.6 | 26.3 | 50.9 | 3.176 g |

[1]HPLC area percent at 450 nm
[2]It was not determined which anhydroluteins and other carotenoids made up this fraction
[3]Results of quantitative HPLC analysis
[4]Addition of the base only after the DMSO-FLORA GLO suspension had reached 80° C.
[5]Addition of the base only after the DMSO-FLORA GLO suspension had reached 90° C.
[6]The higher value was obtained in each case after 0.5 and 1 hour by the addition of an aliquot of the reaction solution to methanol, subsequent stirring of the suspension, filtration and HPLC analysis. Determination of the lower value as already described.

Procedure and results using the starting material XANTOPINA PLUS

The starting material has a composition of 90.9% lutein and 5.3% zeaxanthin in esterified form; the remainder consists of (Z)-isomers of lutein esters and a small amount of anhydrolutein esters. The xanthophyll content of XANTOPINA PLUS is 35.1%. The results of the conversion (without phase transfer catalyst) carried out according to above procedure are compiled in Table 4 hereinafter:

TABLE 4

| Experiment designation | Amount of starting material used | Solvent, amount | Base, conc., amount | Temperature of the reaction mixture | Reaction period (hours) | Relative (%) product composition | | | | | Product amount |
|---|---|---|---|---|---|---|---|---|---|---|---|
| | | | | | | (all-E)-Lutein[1] | (all-E)-Zeaxanthin[1] | Anhydrolutein[2] | (all-E)-Lutein[3] | (all-E)-Zeaxanthin[3] | |
| (y) | 10.0 g | DMSO, 40 ml | KOH, 10.7M, 20 ml | 80° C. | 18 | 41.0 | 53.3 | 3.7 | 20.8 | 27.5 | 4.488 g |
| | | | | | 21 | 40.2 | 54.5 | 3.5 | | | |

1, 2, 3 : see above (End of Table 3)

We claim:

1. A process for the production of zeaxanthin from lutein or an ester thereof which process comprises heating a mixture which contains:
   a) a lutein-containing material comprising lutein or an ester thereof,
   b) an aqueous solution of an alkali hydroxide wherein the alkali hydroxide is present in the solution at a concentration of at least 3M, and
   c) a solvent selected from the group consisting of dimethyl sulphoxide and a liquid aliphatic or aromatic hydrocarbon, at a temperature in the range from about 50° C. to about 120° C., whereby said zeaxanthin is produced from said lutein or ester thereof, with the proviso that when the solvent is the liquid aliphatic or aromatic hydrocarbon, the mixture further comprises an effective amount of a phase transfer catalyst.

2. The process of claim 1 wherein the solvent is dimethyl sulphoxide.

3. The process of claim 2 wherein the alkali hydroxide is present in the mixture in an amount from about 10 to about 450 moles per mole of xanthophyll in the lutein-containing material, the ratio of the volume of the dimethyl sulphoxide to the volume of the alkali hydroxide solution is from about 4:1 to about 1:2, and the total volume of the dimethyl sulphoxide and alkali hydroxide solution is in the range from about 5 to 30 ml per gram of lutein-containing material.

4. The process of claim 3 wherein the alkali hydroxide is present in the mixture in an amount from about 200 to about 250 moles per mole of xanthophylls in said lutein-containing material, the ratio of the volume of the dimethyl sulphoxide to the volume of the alkali hydroxide solution is from about 2.5:1 to about 1:1, and the total volume of the dimethyl sulphoxide and alkali hydroxide solution is in the range from about 6 to 8 ml per gram of lutein-containing material.

5. The process of claim 4 herein the concentration of the alkali hydroxide in the alkali hydroxide solution is in the range from about 7M to about 14M, and the heating is carried out at a temperature in the range from about 80° C. to about 100° C.

6. The process of claim 5 wherein the lutein-containing material is an extract of the yellow or orange blossoms of marigolds.

7. The process of claim 6 wherein the alkali hydroxide is sodium hydroxide.

8. The process of claim 6 wherein the alkali hydroxide is potassium hydroxide.

9. The process of claim 1 wherein the solvent is a liquid aliphatic or aromatic hydrocarbon.

10. The process of claim 9 wherein the alkali hydroxide is present in the mixture in an amount from about 10 to about 450 moles per mole of xanthophyll in the lutein-containing material, the phase transfer catalyst is present in the mixture in an amount from about 0.5 to about 5 moles per mole of xanthophyll in the lutein-containing material, the ratio of the volume of the solvent to the volume of the alkali hydroxide solution is from about 8:1 to about 1:2, and the total volume of the solvent and alkali hydroxide solution is in the range from about 5 to 30 ml per gram of lutein-containing material.

11. The claim 10 wherein the alkali hydroxide is present in the mixture in an amount from about 200 to about 250 moles per mole of xanthophylls in said lutein-containing material, the phase transfer catalyst is present in the mixture in an amount from about 0.5 to about 1.5 moles per mole of xanthophyll in the lutein-containing material, the ratio of the volume of the solvent to the volume of the alkali hydroxide solution is from about 4:1 to about 1:1, and the total volume of the solvent and alkali hydroxide solution is in the range from about 6 to 8 ml per gram of lutein-containing material.

12. The process of claim 11 wherein the concentration of the alkali hydroxide in the akali hydroxide solution is in the range from about 7M to about 14 M, and the heating is carried out at a temperature in the range from about 80° C to about 100° C.

13. The process of claim 12 wherein the lutein-containing material is an extract of the yellow or orange blossoms of marigolds.

14. The process of claim 13 wherein the solvent is pentane, hexane, heptane, petroleum ether, benzene or toluene, and the phase transfer catalyst is tricaprylmethylammonium chloride, tetra(n-butyl)ammonium hydrogen sulphate, benzalkonium chloride, benzyltri(n-butyl)ammonium bromide and tri(n-butyl)methylammonium iodide.

15. The process of claim 14 wherein the solvent is hexane, heptane or high boiling petroleum ether and the phase transfer catalyst is tricaprylmethylammonium chloride.

16. The process of claim 15 wherein the alkali hydroxide is sodium hydroxide.

17. The process of claim 15 wherein the alkali hydroxide is potassium hydroxide.

\* \* \* \* \*

UNITED STATES PATENT AND TRADEMARK OFFICE
CERTIFICATE OF CORRECTION

PATENT NO. : 5,780,693
DATED : July 14, 1998
INVENTOR(S) : Kurt Bernhard and Alfred Giger It is certified that error appears in the above-indentified patent and that said Letters Patent is hereby corrected as shown below:

Column 13, Claim 11, line 1, between "The" and "Claim 10" insert -- process of --.

Signed and Sealed this

Twenty-second Day of September, 1998

Attest:

BRUCE LEHMAN

Attesting Officer

Commissioner of Patents and Trademarks